(12) United States Patent
Joshi et al.

(10) Patent No.: US 7,458,965 B2
(45) Date of Patent: Dec. 2, 2008

(54) FLUID DELIVERY DEVICE HAVING AN ELECTROCHEMICAL PUMP WITH AN ION-EXCHANGE MEMBRANE AND ASSOCIATED METHOD

(75) Inventors: Ashok V. Joshi, Salt Lake City, UT (US); Sai Bhavaraju, Salt Lake City, UT (US); Felix Theeuwes, Los Altos Hills, CA (US); Jeremy C. Wright, Los Altos, CA (US); Strahinja Zecevic, Tustin, CA (US)

(73) Assignee: Microlin, LLC

( * ) Notice: Subject to any disclaimer, the term of this patent is extended or adjusted under 35 U.S.C. 154(b) by 70 days.

(21) Appl. No.: 10/908,804

(22) Filed: May 26, 2005

(65) Prior Publication Data

US 2006/0052768 A1    Mar. 9, 2006

Related U.S. Application Data

(63) Continuation-in-part of application No. 10/137,661, filed on May 1, 2002.

(51) Int. Cl.
*A61K 9/22*  (2006.01)

(52) U.S. Cl. .................. 604/892.1; 604/141
(58) Field of Classification Search ........... 604/890.1, 604/891.1, 892.1
See application file for complete search history.

(56) References Cited

U.S. PATENT DOCUMENTS

| | | | |
|---|---|---|---|
| 2,636,852 A | 4/1953 | Juda et al. | |
| 3,845,770 A | 11/1974 | Theeuwes et al. | |
| 3,894,538 A | 7/1975 | Richter | |
| 3,923,426 A | 12/1975 | Theeuwes | |
| 4,522,698 A | 6/1985 | Maget et al. | |
| 4,549,947 A | 10/1985 | Inoue et al. | |
| 4,552,561 A | 11/1985 | Eckenhoff et al. | |
| 4,593,534 A * | 6/1986 | Bloomfield | 62/201 |
| 4,687,423 A | 8/1987 | Maget et al. | |
| 4,886,514 A * | 12/1989 | Maget | 604/891.1 |
| 4,902,278 A | 2/1990 | Maget et al. | |
| 5,030,216 A | 7/1991 | Theeuwes et al. | |
| 5,167,613 A | 12/1992 | Karami et al. | |
| 5,242,565 A | 9/1993 | Winsel | |
| 5,279,608 A | 1/1994 | Cheikh | |
| 5,312,389 A | 5/1994 | Theeuwes et al. | |
| 5,707,499 A | 1/1998 | Joshi et al. | |
| 5,744,014 A | 4/1998 | Gordon et al. | |

(Continued)

OTHER PUBLICATIONS

"Office Action for U.S. Appl. No, 11/173,813 Dated Jan. 9, 2007", 1-13.

(Continued)

*Primary Examiner*—Nicholas D. Lucchesi
*Assistant Examiner*—Laura A Bouchelle
(74) *Attorney, Agent, or Firm*—David Fonda (57) ABSTRACT

The present invention is directed to an apparatus and method for controllably adjusting a fluid delivery device. The device includes an electrochemical pump capable of transporting a fluid. A displaceable member is positioned between a pump product chamber and a reservoir, wherein the pump product chamber is capable of retaining water generated from the pump. The displaceable member is controllably displaced upon generation of water from the electrochemical pump and the reservoir contains the fluid that is delivered upon displacement of the displaceable member.

38 Claims, 7 Drawing Sheets

U.S. PATENT DOCUMENTS

| | | |
|---|---|---|
| 5,746,064 A | 5/1998 | Tsenter |
| 5,785,688 A | 7/1998 | Joshi et al. |
| 5,788,826 A | 8/1998 | Nyberg |
| 5,891,097 A | 4/1999 | Saito et al. |
| 5,925,030 A | 7/1999 | Gross et al. |
| 5,938,640 A | 8/1999 | Maget et al. |
| 5,951,538 A | 9/1999 | Joshi et al. |
| 6,060,196 A | 5/2000 | Gordon et al. |
| 6,163,720 A | 12/2000 | Gyory et al. |
| 6,287,295 B1 * | 9/2001 | Chen et al. ............... 604/892.1 |
| 6,327,426 B1 | 12/2001 | Joshi et al. |
| 6,450,991 B1 | 9/2002 | Bunt et al. |
| 6,491,684 B1 | 12/2002 | Joshi et al. |
| 6,575,961 B2 | 6/2003 | Joshi |
| 6,576,362 B2 * | 6/2003 | Hanlon ........................ 429/34 |
| 6,872,292 B2 | 3/2005 | Theeuwes et al. |
| 2004/0241528 A1 | 12/2004 | Chiao et al. |
| 2006/0052768 A1 | 3/2006 | Joshi et al. |

OTHER PUBLICATIONS

"Office Action for U.S. Appl. No. 10/137,661 Dated Dec. 20, 2006", 1-9.

Bouchelle, Office Action for U.S. Appl. No. 10/137,661 sent Apr. 24, 2006, 1-7.

Anderson, Office Action for U.S. Appl. No. 11/173,813 sent Sep. 13, 2007, 1-12.

Greene, International Search Report for PCT/US06/22502 sent May 21, 2007, 1-2.

Greene, Written Opinion for PCT/US06/22502 sent May 21, 2007, 1-3.

Copenhaver, International Search Report for PCT/US06/20570 sent Nov. 22, 2006, 1-2.

Copenheaver, Written Opinion for PCT/US06/20570 sent Nov. 22, 2006, 1-4.

* cited by examiner

FLUID DELIVERY DEVICE HAVING AN ELECTROCHEMICAL PUMP WITH AN ION-EXCHANGE MEMBRANE AND ASSOCIATED METHOD

STATEMENT OF RELATED APPLICATIONS

This application is a continuation-in-part of U.S. patent application Ser. No. 10/137,661, filed May 1, 2002, which is incorporated herein by reference.

FIELD OF INVENTION

The present invention relates in general to a fluid delivery device that includes an electrochemical pump for controllably delivering small volumes of fluid with high precision and accuracy. The fluid delivery rate of the device can also be changed during operation by simple means

BACKGROUND ART

In many medical situations, it may be necessary or at least desirable to deliver small amounts of fluids and/or chemical agents over a relatively long period of time. Such fluids may include, biologicals, drugs, lubricants, fragrant fluids, and chemical agents. A common example of such an application is the gradual administration of a pharmaceutical agent into the human body. A very common and traditional apparatus for the gradual administration of fluid into the human body is an intravenous administration set in which gravity induced hydrostatic infusion dispenses a fluid from a familiarly suspended bottle or bag above the patient.

Other methods for the gradual administration of fluids have been devised to eliminate the need for suspending the fluid above the patient and thereby provide the patient with greater mobility. One such method utilizes a diffusion controlled delivery pump wherein the fluid diffuses through a membrane at a constant rate. The rate of delivery may be adjusted by varying the nature of the membrane and the concentration of the solution in contact with the membrane, e.g., a transdermal drug delivery patch. Additional transdermal technologies include: iontophoresis wherein low voltage electrical current is utilized to drive charged drugs through the skin; electroporation wherein short electrical pulses of high voltage is utilized to create transient aqueous pores in the skin; sonophoresis wherein low frequency ultrasonic energy is utilized to disrupt the stratum corneum; and thermal energy wherein heat is utilized to make the skin more permeable and to increase the energy of drug molecules. Even magnetic energy, or magnetophoresis, has been investigated as a means to increase drug flux across the skin. Of these transdermal technologies, only iontophoresis has been successfully developed into a marketable product, albeit for local pain relief. A transdermal system may not be the preferred method for gradually administering fluids in every case and various factors should be considered that may affect its usefulness, such as: the adhesive utilized to secure the system to the individual may not adhere well to all types of skin; some drug formulation may cause skin irritation or allergy; the transdermal system may be uncomfortable to wear or too costly; and some drugs that require high blood levels (low potency) cannot be properly administered.

A mechanical pump dispenser is another mechanism for gradually administering fluids to an individual. The mechanical pump dispenser uses various types of mechanical pumps to expel the fluid from a reservoir. Some processes incorporating a mechanical pump dispenser include: a continuous intravenous infusion pump system, for example from Intevac Inc.; an epidural infusion system; and a subcutaneous infusion system, e.g., utilizing a portable insulin infusion pump. An externally worn pump is also conventionally used with a transcutaneous catheter, however, the external pump is often bulky and inconvenient because it is typically strapped onto the wearer, or carried on a belt or in a harness. A common drawback of the mechanical pump is that the required entry site into the body is susceptible to infection. In addition, most mechanical pumps are designed to deliver relatively large quantities of fluid and do not effectively dispense small volumes or for longer periods of time.

Other fluid delivery processes utilize pressure to administer a fluid to the individual, For instance, a charged reservoir dispenser stores a fluid under pressure in a flexible reservoir and then selectively expels the fluid by the force of internal reservoir pressure—the rate of release often being regulated by a plurality of complex valve systems. A pressurized gas dispenser uses a pressurized gas to expel the fluid. And an osmotic dispenser relies on a solute that exhibits an osmotic pressure gradient against water to dispense the fluid. The OROS® system produced by ALZA Corporation is an example of an osmotically driven system in which osmosis is the energy source for drug delivery. In the OROS® system, the drug solution flows from the tablet at a constant zero-order rate as the tablet progresses through the gastro-intestinal (GI) tract until the entire solid drug in the core is dissolved or until the unit is eliminated. In vivo and in vitro testing has shown that the delivery rate is independent of GI motility, pH, and food in the gastro-intestinal tract. The release of the drug is controlled by the solubility of the drug in gastric fluid, the osmotic pressure of the core formulation, and the dimensions and permeability of the membrane.

Although the above-identified fluid administration device types or techniques are available, there remains an ongoing desire for improvements therein. For example, the gradual administration of a pharmaceutical agent into the human body often requires the continuous delivery of small quantities of fluids over a period of many hours. In such an application, it is desirable that the fluid dispenser be highly accurate and reliable, sufficiently small and lightweight to be portable, and convenient and easy to use. In general, implantable drug delivery pumps and systems allow for the direct delivery of the pharmaceutical agent to the desired site, thus maximizing the impact of the drug while minimizing unwanted side effects in other parts of the body.

There are a number of implantable drug delivery pumps and systems presently being used. One widely used implant is the large capacity (18 mL) programmable electromechanical SynchroMed® pump. While applicable in a number of therapies, several drawbacks of the SynchroMed® pump are its cost, the overall cost of the therapy, and that surgery is required for placement of the large pump.

Smaller sized implantable drug delivery pumps are also available; such as the osmotic pump of the DUROS® system. In operation, water is imbibed osmotically through a membrane into a salt chamber pressurizing a piston to expand into a drug chamber to force a drug out through a delivery orifice. The driving force behind the drug delivery of this pump is osmotic pressure, which can be as high as 200 atmospheres depending on the salt used, even though the pressure required to pump the drug from the device is small and the drug delivery rate remains constant as long as some excess undissolved salt remains in the salt chamber. In comparison with mechanically driven devices, osmotic systems are small, simple, reliable, and less expensive to manufacture. Because of the small size of the osmotic system, it can be implanted during a simple procedure in the physician's office. On the other hand, the fixed delivery rate of the osmotic pump in not adjustable during its operation.

Gas generating devices that are both portable and accurate for dispensing small volumes have also been used in drug delivery systems. These gas-generating methods include galvanic cells and electrolytic cells. In galvanic gas generating cells, hydrogen or oxygen gas is formed at the cathode or anode, respectively, as a result of a reaction between a metal or metal oxide and an aqueous electrolyte. By definition, a galvanic cell is an electrochemical cell that requires no externally applied voltage to drive the electrochemical reactions. Typically, the anode and cathode of the galvanic cell are connected through a resistor that regulates the current passed through the cell, and in turn, directly regulates the production of gas that exerts a force on a diaphragm or piston—thereby expelling the drug. A number patents have disclosed delivery systems based on the use of galvanic hydrogen generating cell, e.g., U.S. Pat. Nos. 5,951,538; 5,707,499; and 5,785,688. In the cells disclosed in these patents, a zinc anode reacts with an alkaline electrolyte producing zinc oxide and water molecules are reduced on porous carbon electrode producing gaseous hydrogen. Additionally, U.S. Pat. Nos. 5,242,565 and 5,925,030 disclose a galvanic oxygen-generating cell that is constructed much like a zinc/air button cell, wherein a reducible oxide is reduced at the cathode while hydroxyl ions are formed. The hydroxyl ions oxidize at the anode and release oxygen.

In contrast to the galvanic cell, an electrolytic cell requires an external DC power source to drive the electrochemical reactions. When voltage is applied to the electrodes, the electrolyte gives off a gas that exerts a force on a diaphragm or piston—thus expelling the fluid. Three types of electrolytic gas generating cells have been proposed for use in fluid delivery devices. A first type is based on water electrolysis requiring an operating voltage over 1.23 V. A second type, also known as oxygen and hydrogen gas pumps, requires a lower DC voltage than that utilized in water electrolysis systems. Both of these cell types utilize an ion exchange polymer membrane. A third type of gas generating electrolytic cell is based on the use of an electrolytically decomposable chemical compound that produces a reduced metal at the cathode, and generates gaseous oxygen by oxidation of water at the anode.

U.S. Pat. No. 5,891,097 discloses an electrochemically driven fluid dispenser based on the electrolysis of water. In this dispenser, water is contained in an electrochemical cell in which porous metal electrodes are joined to both sides of a solid polymer cation exchange membrane, and both of the two electrodes are made to contact with the water so as to use oxygen or hydrogen generated from an anode or cathode respectively, upon current conduction. Thus, hydrogen, oxygen, or a gas mixture of hydrogen and oxygen—generated by electrolysis of water when a DC current is made to flow between the electrodes—is used as a pressurization source of the fluid dispenser.

Electrochemical oxygen and hydrogen pumps are constructed in a similar manner to the above-discussed water electrolysis cell and are described in several U.S. patents, e.g., U.S. Pat. Nos. 5,938,640; 4,902,278; 4,886,514; and, 4,522, 698. Electrochemically driven fluid dispensers disclosed within these patents have an electrochemical cell in which porous gas diffusion electrodes are joined respectively to the opposite surfaces of an ion exchange membrane containing water functioning as an electrolyte. The electrochemically driven fluid dispenser uses such a phenomenon that when hydrogen is supplied to an anode of the electrochemical cell and a DC current is made to flow between the anode and the cathode, the hydrogen becomes hydrogen ions at the anode. When the produced hydrogen ions reach the cathode through the ion exchange membrane, an electrochemical reaction arises to generate gaseous hydrogen thereat. Since the net effect of these processes is the transport of hydrogen from one side of the membrane to the other, this cell is also called a hydrogen pump. The hydrogen generated and pressurized at the cathode is used as a driving source for pushing a piston, a diaphragm, or the like.

Alternatively, oxygen may be used in place of hydrogen as a reactant in this type of electrochemical cell, wherein the cell then acts as an oxygen pump. Thus, oxygen is reduced on one side of a water-containing electrolytic cell and water is oxidized on the opposite side to generate molecular oxygen, wherein the molecular oxygen so generated is used as the propellant to force liquid from an adjacent reservoir.

A gas generating electrolytic cell using an electrolytically decomposable chemical compound that produces a reduced metal at the cathode, and generates gaseous oxygen by water oxidation at the anode, is disclosed in U.S. Pat. No. 5,744, 014. This cell generally includes a graphite anode, an aqueous electrolyte, and a copper hydroxide cathode. As electrical current passes through a circuit in which the cell is connected, copper is plated out in the cathode and oxygen is released at the anode. To ensure storage stability, an active cathode material is selected such that the cells require an applied voltage for the electrochemical reactions to proceed. A battery cell is provided in the circuit to drive the current through the gas-generating cell. The rate of oxygen generated at the anode is directly proportional to the current and acts as a pressurizing agent to perform the work of expelling a fluid from a bladder or other fluid-containing reservoir, which has a movable wall that is acted upon as the gas is generated.

While the above-identified electrochemically driven fluid delivery devices are operable for certain applications, they are not optimal for others. In particular, gas generating cell based pumps are sensitive to temperature and atmospheric pressure. For this reason, osmotic and electroosmotic pumps are often more appropriate.

The osmotic pump involves imbibing water or another driving fluid. The pump consists of three chambers: a salt chamber, a water chamber, and a fluid chamber. The salt and water chambers are separated by a semi-permeable membrane. This configuration creates a high osmotic driving force for water transport across the membrane. This membrane is permeable to water, but impermeable to salt. The fluid chamber is separated from the other two chambers by a flexible diaphragm. Water imbibes osmotically into the salt chamber creating substantial hydrostatic pressures, which in turn exert a force on the diaphragm—thus expelling the fluid. The use of osmotic pumps is typically limited to applications requiring constant fluid delivery. In order to vary the fluid flow, it is typically necessary to provide numerous osmotic pumps with differing outputs. The osmotic pump also requires charging—the time required for liquid to diffuse through the semipermeable membrane and begin dissolving the osmagent at steady state—which in turn delays delivery of the active and further limits its suitability for instantaneous or emergency use. The fluid delivery rate of the osmotically driven device can neither be changed nor is it possible to shut-off the delivery of the active after commencement of delivery. Hence, it is preferable to utilize a device that can be rapidly switched-on and allows the delivery rate to be changed by a remote controlling mechanism.

An electroosmotic pump is an electrolytic cell having a permselective ion exchange membrane and therefore requires an external DC power source to drive the electrode reactions. U.S. Pat. No. 3,923,426 discloses an electrochemically driven fluid dispenser based on electroosmotic fluid transport. The pump comprises a plastic housing having a fluid inlet and outlet, a pair of spaced silver-silver chloride electrodes disposed in the housing and connected to a D.C. power source, a porous ceramic plug that has a high zeta potential relative to the fluid, a cation exchange membrane positioned on each side of the ceramic plug between it and the electrode facing it, and a passageway in the housing extending from the fluid inlet to one side of the plug and from the other side of the plug to the outlet. When a potential difference is applied across anode and cathode, the transport fluid will flow through the porous plug from the anode to the cathode. One particular disadvantage of this electroosmotic pump with a porous plug is that the delivery pressures are very low, well below 0.5 ATM. In addition, any ions in the driving fluid will substantially affect the zeta potential and reduce the electroosmotic flow. Another disadvantage of this electroosmotic pump is that it requires an external D.C. power source that lessens the overall volume efficiency of the fluid delivery device.

Accordingly, there is a need for an implantable volume efficient fluid dispenser including a highly accurate programmable delivery mechanism that can be quickly adjusted to change its delivery rate as desired. The delivery mechanism occupies a small portion of the fluid dispenser, is capable of delivering small volumes of fluid with precision and accuracy, and is impervious to barometric pressure and temperature.

SUMMARY OF THE INVENTION

The present invention is directed to a controlled adjustable water transporting fluid delivery device, comprising: (a) an electrochemical pump, wherein the pump is capable of transporting water; (b) a pump product chamber, wherein the pump product chamber is capable of retaining water generated from the pump—including at high pressure; (c) a displaceable member positioned between the pump product chamber and a reservoir, wherein the displaceable member is controllably displaced upon generation of water from the electrochemical pump; (d) a reservoir, wherein the reservoir is capable of containing a fluid that is delivered upon displacement of the displaceable member; and, (e) a housing for containing the pump, the pump product chamber, the displaceable member, and a reservoir. Preferably, the displaceable member is selected from the group consisting of a piston, bladder, bellows, diaphragm, plunger, and combinations thereof. Additionally, the fluid delivery device can also include a catheter for delivering fluid at a desired location.

In a preferred embodiment of the present invention, a pump engine comprises a protective porous separator, a first electrode, a second electrode, an ion exchange membrane, and an electric controller. In this embodiment, the pump may further include an activation switch to start the fluid delivery; a controller, e.g., an electrical resistor or circuit that may or may not be controlled remotely, capable of enabling a faster fluid delivery start-up and shut-off, and quicker adjustability; and a support member(s) for providing physical support for the membrane.

In a further aspect of the present invention, the reservoir includes one or more apertures, e.g., outlet and filling/refilling port, and contains a fluid selected from the group consisting of a biological, drug, lubricant, fragrant fluid, chemical agent, and mixtures thereof.

In yet another further aspect of the present invention, a process is provided for delivering a fluid, comprising the steps of: (a) providing a fluid delivery device having an electrochemical water transporting pump; (b) transporting water through the water transporting pump, thereby expanding a volume of a pump product chamber; (c) generating sufficient pressure from the expanded pump product chamber; and, (d) displacing a displaceable member wherein a fluid is controllably expelled from the fluid delivery device.

An object of the present invention is to provide a fluid delivery device that includes a volume efficient fluid dispenser wherein the delivery mechanism occupies a small part of the overall device.

Another object of the present invention is to provide a fluid delivery device that is small, portable, and capable of being implanted.

A further object of the present invention is to provide a fluid delivery device that is highly accurate and capable of precisely delivering small volumes of fluid.

A still further object of the present invention is to provide an adjustable fluid delivery device that can be controlled to quickly change the delivery rate.

Yet another object of the present invention is to provide a fluid delivery device that utilizes few moving parts, is simple to construct, and is less susceptible to mechanical failure.

Yet a still further object of the present invention is to provide a fluid delivery device that does not utilize compressible components and thus enables the device to operate at different altitudes and a wide range of barometric pressures.

BRIEF DESCRIPTION OF THE DRAWINGS

The invention will now be described with reference to the drawings wherein.

DETAILED DESCRIPTION OF THE INVENTION

While this invention is capable of embodiment in many different forms, there is shown in the drawings and will herein be described in detail several specific embodiments the understanding that the present disclosure is to be considered as an exemplification of the principles of the invention and is not intended to limit the invention to the embodiments illustrated.

It is to be understood that like or analogous elements and/or components—referred to herein—may be identified throughout the drawings with like reference characters.

Figure 1:
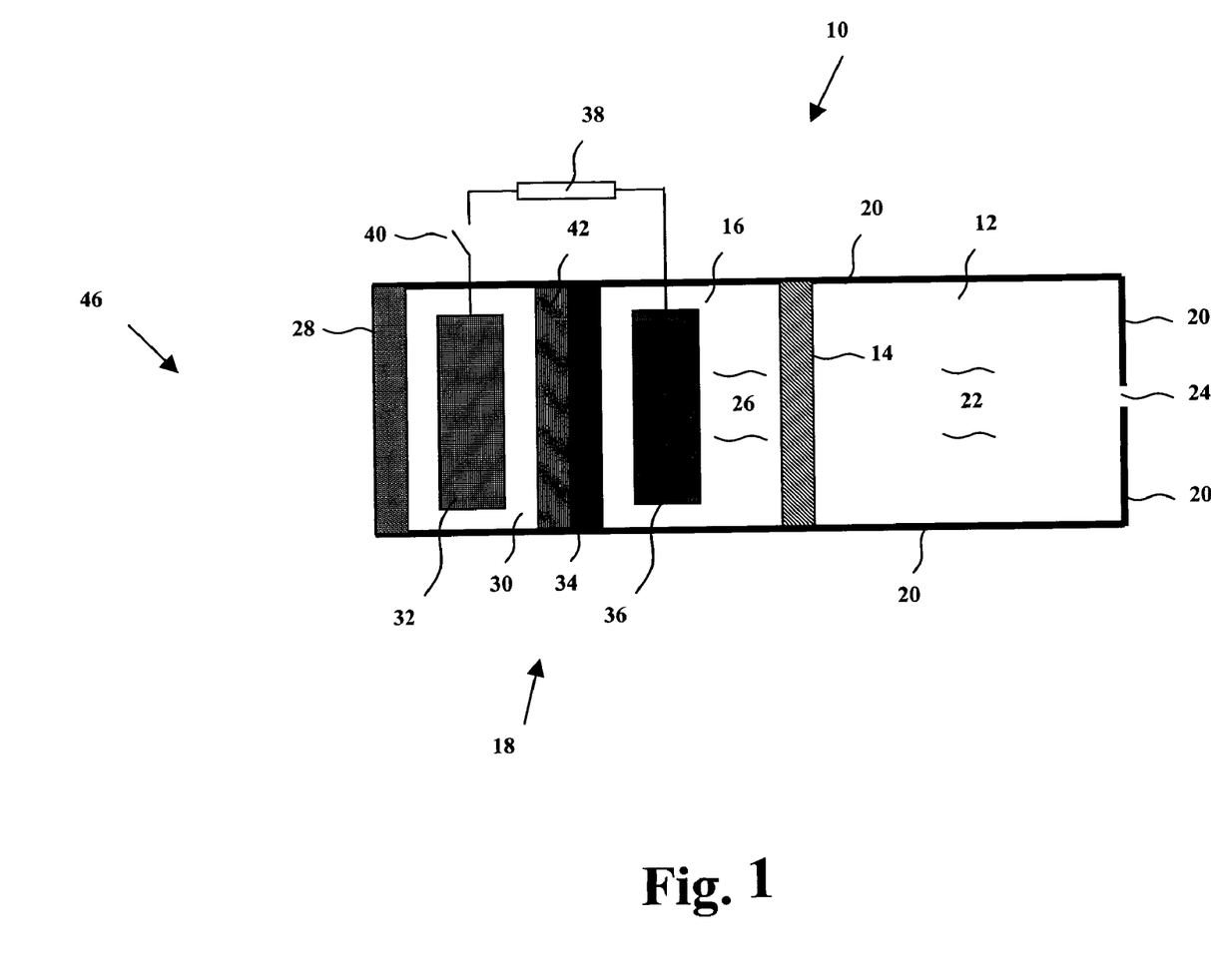
FIG. 1 is a cross-sectional schematic representation of a fluid delivery device having an anionic exchange membrane fabricated in accordance with the present invention.

Referring now to the drawings and to FIG. 1 in particular, a first embodiment of the present invention is shown wherein a fluid delivery device 10 comprises a reservoir 12, a displaceable member 14, an electrochemical pump product chamber 16, an electrochemical pump 18, and a housing 20. It is to be further understood that FIG. 1 is merely a schematic representation of the fluid delivery device 10 of the present invention and as such, some of the components have been distorted from their actual scale for pictorial clarity.

The reservoir 12 is capable of containing a fluid 22, such as a biological, drug, lubricant, fragrant fluid, chemical agent, or mixtures thereof, which is delivered upon displacement of the displaceable member 14. It will be understood that the term "fluid" is herein defined as a liquid, gel, paste, or other semi-solid state material that is capable of being delivered out of a reservoir. The reservoir 12 may include one or more apertures 24 for directing delivery of the fluid 22 from the fluid delivery device 10. The reservoir 12 may be fabricated from any one of a number of materials, including, for example, metal, glass, natural and synthetic plastic, and composites.

The displaceable member 14 is positioned between the reservoir 12 and the electrochemical pump product chamber 16. The displaceable member 14 is shown in FIG. 1 as comprising a piston, however, other displaceable members that would be known to those having ordinary skill in the art having the present disclosure before them are likewise contemplated for use; including, but not limited to: a bladder, a diaphragm, a bellows, and a plunger.

The electrochemical pump product chamber 16 is positioned between the displaceable member 14 and the electrochemical pump 18, and is capable of containing water 26 that—as will be discussed in greater detail below—is controllably generated during operation of the electrochemical pump 18. Similar to the reservoir 12, the electrochemical pump product chamber 16 may be fabricated from any one of a number of materials, such as metal, glass, natural and synthetic plastic, composites, etc.

The electrochemical pump 18 shown in FIG. 1 includes a protective porous separator 28, an auxiliary electrode compartment 30, an auxiliary electrode 32, an ion exchange membrane 34, an active electrode 36, an electric resistor 38, an activation switch 40, and a support member(s) 42.

The protective porous separator 28 is positioned at an end of fluid delivery device 10 distal from the reservoir 12. The protective porous separator 28 is generally permeable to $H_2O$ molecules from the body, and its cooperation with saline from the auxiliary electrode compartment 30—e.g., metal halides, such as NaCl—enables the water from an external source 46—e.g., an inside of a living being's body—to diffuse or migrate into the auxiliary electrode compartment 30. The protective porous separator 28 may be fabricated from any one of a number of materials; including, but not limited to metal, glass, natural and synthetic plastic, and composites. Additionally, a porous protective gel may be used to serve the purpose of the separator. The protective porous separator or protective porous gel is generally permeable to $H_2O$ molecules or saline. The protective porous separator or gel may also include a water or saline reservoir.

Alternatively, the use of the protective porous separator 28 is not required and the auxiliary electrode compartment 30 may be self-contained without the presence of the protective porous separator. In such an embodiment, the auxiliary electrode can be exposed directly to fluid and the necessary amount of water is carried in the auxiliary electrode compartment 30 without any migration of water from external source 46.

In the first embodiment of the present invention, an anionic exchange membrane, the auxiliary electrode 32, the anionic exchange membrane 34, and the active electrode 36 are respectively positioned adjacent to the protective porous separator 28. The auxiliary electrode 32 is a porous cathode pellet that can be readily reduced when coupled with the active metal anode 36. The auxiliary electrode 32 may be fabricated from porous silver chloride, manganese dioxide, or other materials that can be readily reduced or may catalyze reduction reaction—e.g., reduction of oxygen or evolution of gaseous hydrogen from water—when coupled with the active metal anode. The active metal anode 36 is a solid pellet, mesh, or metal powder type electrode fabricated from zinc, iron, magnesium, aluminum, or another corrosion stable metal or alloy. Although not shown, the auxiliary electrode 32 may include a conventional current collector, such as screen, mesh, or wire current collector fabricated from silver, titanium, platinum, or another corrosion stable metal. The active metal anode 36 may also include a conventional current collector, such as a screen, mesh or wire current collector fabricated from the same metal as that of the active metal anode; or it may be fabricated from other metals such as brass, which is coated with the same metal as is the active anode metal. While specific examples of electrode materials and current collectors have been disclosed, for illustrative purposes, it is to be understood that other electrode materials known to those with ordinary skill in the art having the present disclosure before them are likewise contemplated for use.

The anion exchange membrane 34 is positioned between the first electrode 32 and the second electrode 36. The anion exchange materials from which the membrane 34 may be made are well known in the art and do not require extensive elaboration. In brief, these materials are cross-linked polymer resins of the strong base type. Preferred resins are the copolymers of styrene and di-vinyl benzene having quaternary ammonium ion as the charge group, which have a high selectivity for chloride ions and high resistance to organic fouling. Such anionic membranes are, for example, Neosepta-type membranes, which are commercially available from AMERIDIA (www.ameridia.com).

In an alternate second embodiment of the present invention incorporating a cationic exchange membrane, the auxiliary electrode 32, the cationic exchange membrane 34, and the active electrode 36 are respectively positioned adjacent to the protective porous separator 28. The auxiliary electrode 32 is a solid pellet, mesh, or metal powder type electrode that is fabricated from zinc, iron, magnesium, aluminum, or another corrosion stable metal or alloy. The active metal anode 36 is a porous cathode pellet that can be readily reduced when coupled with the active metal anode 36. The auxiliary electrode 32 may be fabricated from porous silver chloride, manganese dioxide, or other materials that can be readily reduced, or may catalyze reduction reaction—e.g., reduction of oxygen or evolution of gaseous hydrogen from water—when coupled with the active metal anode. Although not shown, the auxiliary metal anode 32 may also include a conventional current collector, such as screen, mesh, or wire current collectors fabricated from the same metal as that of the active metal anode 36; or it may be fabricated from other metals such as brass, which is coated with the same metal as is the active anode metal. The active electrode 36 may include a conventional current collector such as screen, mesh, or wire current collectors fabricated from silver, titanium, platinum, or another corrosion stable metal. While specific examples of electrode materials and current collectors have been disclosed for illustrative purposes, it is to be understood that other electrode materials known to those with ordinary skill in the art having the present disclosure before them are likewise contemplated for use.

Referring to FIG. 1, the cation exchange membrane 34 is positioned between the first electrode 32 and the second electrode 36. The cation exchange materials from which the membrane 34 may be constructed are well known in the art and do not require extensive elaboration. In brief, these materials are cross-linked polymer resins of the strong base type. Some preferred resins include copolymers of styrene and di-vinyl benzene having sulfonate ion as the charge group, which have a high selectivity for sodium ions. Such commercial cationic membranes, e.g., Nafion type membranes, are available from Dupont®.

The electrical control circuit 38 is connected to the electrodes via conventional electrical conduit and as will be discussed in greater detail below, directly controls the rate of water transfer from the external source 46 to the electrical pump product chamber 16. The support members 42 are highly porous solid disk materials that provide mechanical rigidity for the ion exchange membrane and allow water to transport through it. The support members 42 can be made of hard plastic; ceramic; glass or corrosion stable metals, e.g., titanium; or a combination thereof.

In operation, the fluid delivery device 10 can deliver fluid 22 in accordance with the following process. Initially, the activation switch 40 is actuated, whereupon an electrical circuit is complete and causes electrode reactions to take place at the electrodes 32, 36, and water to be extracted from the external environment 46; and, ultimately to be driven across ion exchange membrane 34 into the electrical pump product chamber 16. Thus, water from the external environment 46—such as a human body—diffuses through the protective porous separator 28 and into the first electrode compartment 30.

In the first embodiment of the present invention wherein the first electrode 32 is made of silver chloride and the second electrode 36 is made of zinc, the following reactions occur. At first, the electrode silver chloride is reduced to metallic silver, thus releasing chloride ions into solution according to the equation:

$$2AgCl + 2e^- \rightarrow 2Ag + 2Cl^- \tag{1}$$

The chloride ions subsequently formed are dissolved in water and migrate under the influence of the electric field through the ion exchange membrane 34 towards the second electrode 36 in the electrical pump product chamber 16. At the second electrode 36, zinc is dissolved according to the equation:

$$Zn \rightarrow Zn^{2+} + 2e^- \tag{2}$$

The zinc ions thus formed react with incoming chloride ions forming zinc chloride according to the equation:

$$Zn^{2+} + 2Cl^- \rightarrow ZnCl_2 \tag{3}$$

In addition to the electrochemical formation of zinc chloride according to the equation (3), during passage of the chloride ions through the membrane, water is entrained with the chloride ions so that at the opposite side of the membrane, an additional amount of water is produced. This water transport is known in the art as electroosmotic transport. Since the anionic membrane is selective for anions, only anions can pass through the membrane. Therefore, water may be transported through the membrane only in one direction.

The steady buildup of ion concentration in the electrochemical pump product chamber 16 due to the continuous formation of zinc chloride induces further water transport through osmotic effect. However, the ion-exchange membrane allows back diffusion of the zinc chloride molecules from the electrochemical product chamber 16 to the first electrode chamber 30. The extent of back-diffusion depends on the properties of the ion-exchange membrane and the concentration difference between the electrochemical product chamber 16 and the auxiliary electrode compartment 30. Thus, an equilibrium concentration of zinc chloride is established in the electrochemical pump product chamber 16 resulting in water transport via osmotic effect. A steady state flux of water transport into the electrochemical pump product chamber 16 by combined electroosomotic and osmotic effects is thus established. It must be noted that the osmotic flux is the result of the electro-osmotic flux, which establishes the necessary concentration gradient. Therefore, the osmotic flux can be modified by virtue of modifying the electroosmotic driving force. This is not possible with osmosis based devices and so their delivery rate is not adjustable. The water molecules transported into the electrochemical pump product chamber 16 generate pressure within the electrochemical pump product chamber. The pressure build-up causes some back transport of water from the electrochemical pump product chamber 16 to the auxiliary electrode compartment 30.

The steady state flux obtained for a given ion-exchange membrane can be expressed in terms of the following mathematical equation:

$$J_{Steady\ State\ Flux} = J_{eof} + J_{of} - J_{bdf} - J_{hf} \tag{I}$$

Where,
$J_{eof}$=electroosmotic flux
$J_{of}$=osmotic flux
$J_{bdf}$=back diffusion flux
$J_{hf}$=hydraulic flux

In the second embodiment of the present invention wherein the first electrode 32 is made of zinc and the second electrode 36 is made of silver chloride, the following reactions take place. At first, the electrode zinc is dissolved according to the equation:

$$Zn \rightarrow Zn^{2+} + 2e^- \tag{4}$$

Sodium ions present in the saline solution migrate under the influence of the electric field through the ion exchange membrane 34 towards the second electrode 36 in electrical pump product chamber 16. At the second electrode 36, silver chloride is reduced to metallic silver releasing chloride ions into solution according to the equation:

$$2AgCl + 2e^- \rightarrow 2Ag + 2Cl^- \tag{5}$$

The migrated sodium ions react with the chloride ions forming sodium chloride according to the equation:

(6)

In addition to the electrochemical formation of sodium chloride according to the equation (6), during passage of the sodium ions through the membrane, water is electroosmotically transported with sodium ions so that at the opposite side of the membrane, an additional amount of water is produced. Since the cationic membrane is selective for cations, only cations can pass through the membrane. Therefore, water may be transported through the membrane only in one direction.

Due to the continuous formation of sodium chloride, the steady buildup of ion concentration in the electrochemical pump product chamber 16 induces further water transport through osmotic effect. However, the ion-exchange membrane allows back diffusion of sodium chloride molecules from the electrochemical product chamber 16 to the first electrode chamber 30. The extent of back-diffusion depends on the properties of the ion-exchange membrane and the concentration difference between the electrochemical product chamber 16 and the auxiliary electrode compartment 30. Thus, an equilibrium concentration of sodium chloride is established in the electrochemical pump product chamber 16 resulting in water transport by the osmotic effect. A steady state flux of water transport into the electrochemical pump product chamber 16 is established by the combined electroosomotic and osmotic effects. It must be noted that the osmotic flux is the result of the electro-osmotic flux, which establishes the necessary concentration gradient. Therefore, the osmotic flux can be modified by virtue of modifying the electroosmotic driving force. This is not possible with osmosis based devices and so their delivery rate is not adjustable. The water molecules transported into the electrochemical pump product chamber 16 generate pressure within the electrochemical pump product chamber 16. The pressure buildup causes some back transport of water from the electrochemical pump product chamber 16 to the auxiliary electrode compartment 30. The steady state flux obtained for a given ion-exchange membrane can be expressed in terms of the same mathematical equation I shown above.

Both embodiments of the present invention discussed above are capable of generating high pressure within the electrochemical pump product chamber 16. High pressure is desired to deliver viscous formulations and to also produce delivery that is less sensitive to the ambient pressure changes.

Figure 6:
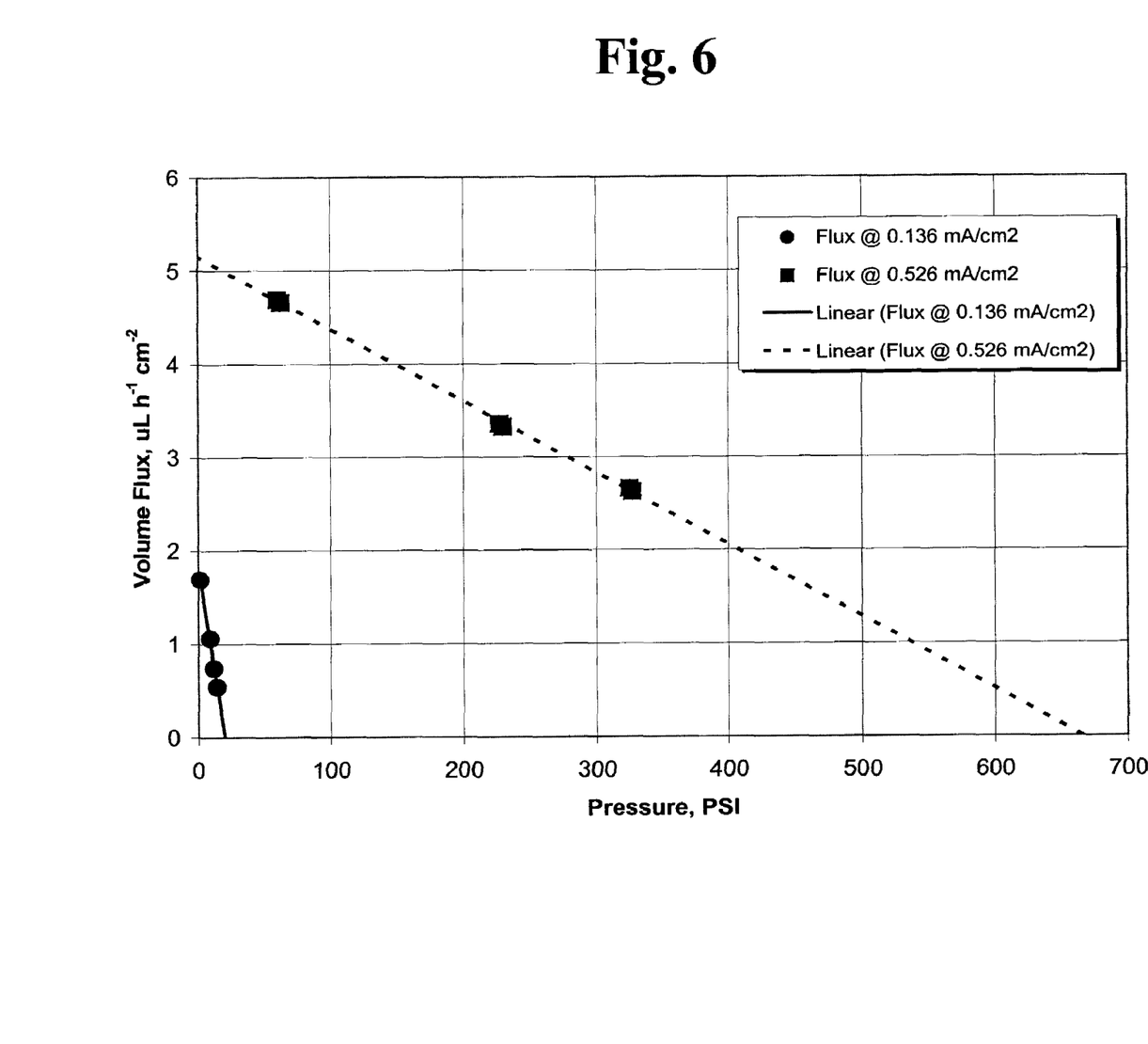
FIG. 6 is a graph of volume flux vs. pressure applied to the electrochemical product chamber at two different current density values for a fluid delivery device having an anionic exchange membrane fabricated in accordance with the present invention; Cell parameters: Neosepta® AFN ion exchange membrane, solid zinc anode, silver chloride cathode, 0.9% NaCl electrolyte; and, FIG. 7 is a graph of volume flux vs. pressure applied to the electrochemical product chamber at two different current density values for a fluid delivery device having an cationic exchange membrane fabricated in accordance with the present invention; Cell parameters: NAFION® 117 cation exchange membrane, solid zinc anode, silver chloride cathode, 0.9% NaCl electrolyte.
Figure 7:
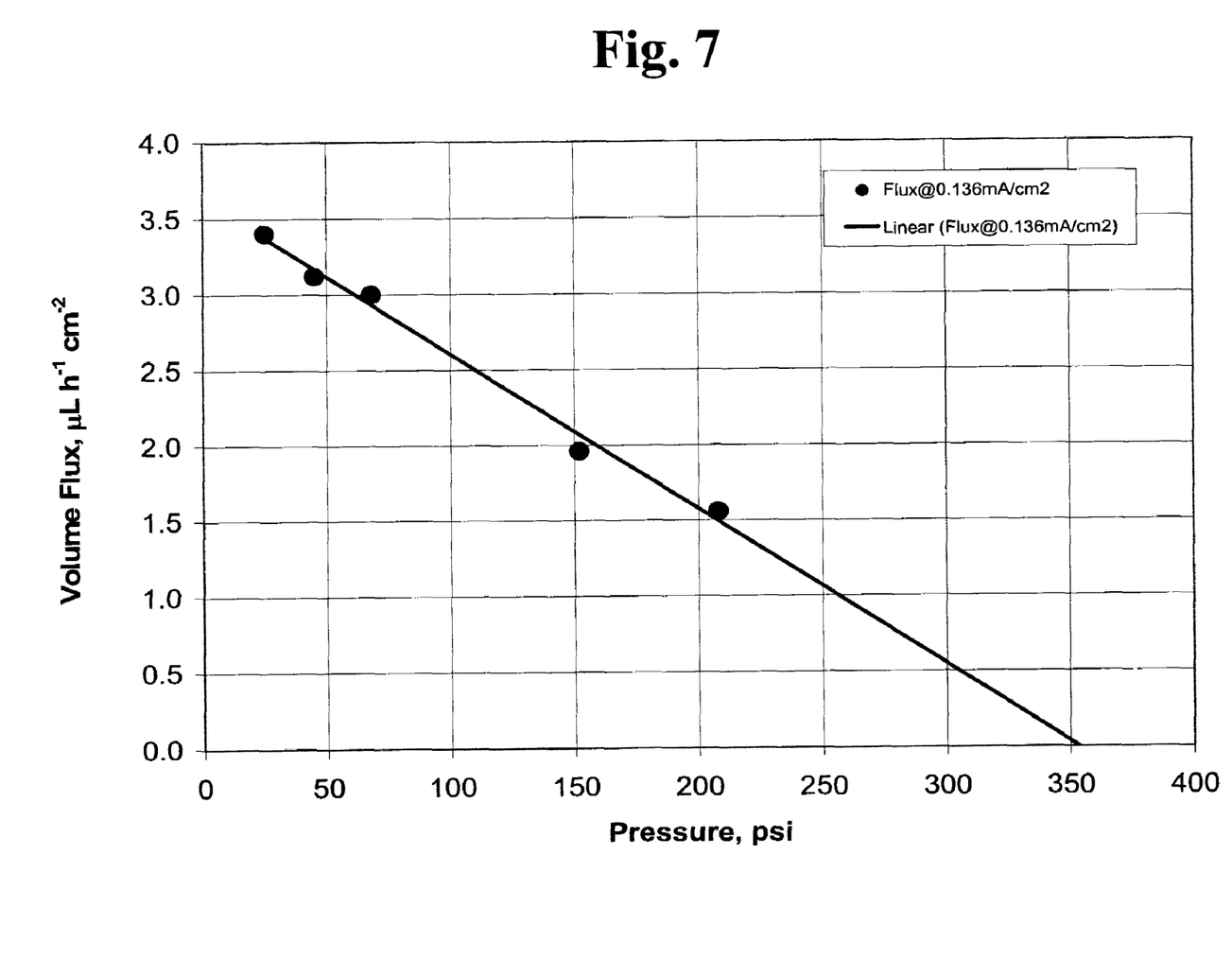

The pressure generated by the first embodiment of the present invention discussed above is shown in FIG. 6 wherein the maximum pressure ($P_{max}$, the pressure at which the flux becomes zero) that can be achieved is 20 psi at 0.136 mA/cm². Operation at 3.8 times the current density (0.525 mA/cm²) provided a $P_{max}$ of 700 psi. In the case of the second embodiment of the present invention, FIG. 7 shows $P_{max}$ to be 350 psi at 0.136 mA/cm².

The generated pressure, in turn, imparts a force upon displaceable member 14—the only movable component. The displaceable member 14 is displaced laterally away from electrochemical pump product chamber 16, which controllably expels fluid from the reservoir 12. It is to be understood that the above-identified device and process enables a controlled delivery of a fluid over an extended period of time at a relatively precise and accurate rate inasmuch as the water transported is proportional to the current, which in turn depends on the value of the resistor, or on the signal output from the electrical controller 38. Therefore, the fluid delivery rate of the device is controlled by selection of the 38 or on the signal output from the electrical controller and not by the rate at which water is permitted to enter the housing via convection action of the protective porous separator 28. It is also to be understood that the fluid delivery rate, or a fluid delivery rate profile, e.g., pulsing, can be facilely varied by other means, including, but not limited to, selecting resistors with different resistance values or by changing the signal output from the electrical controller.

Figure 2:
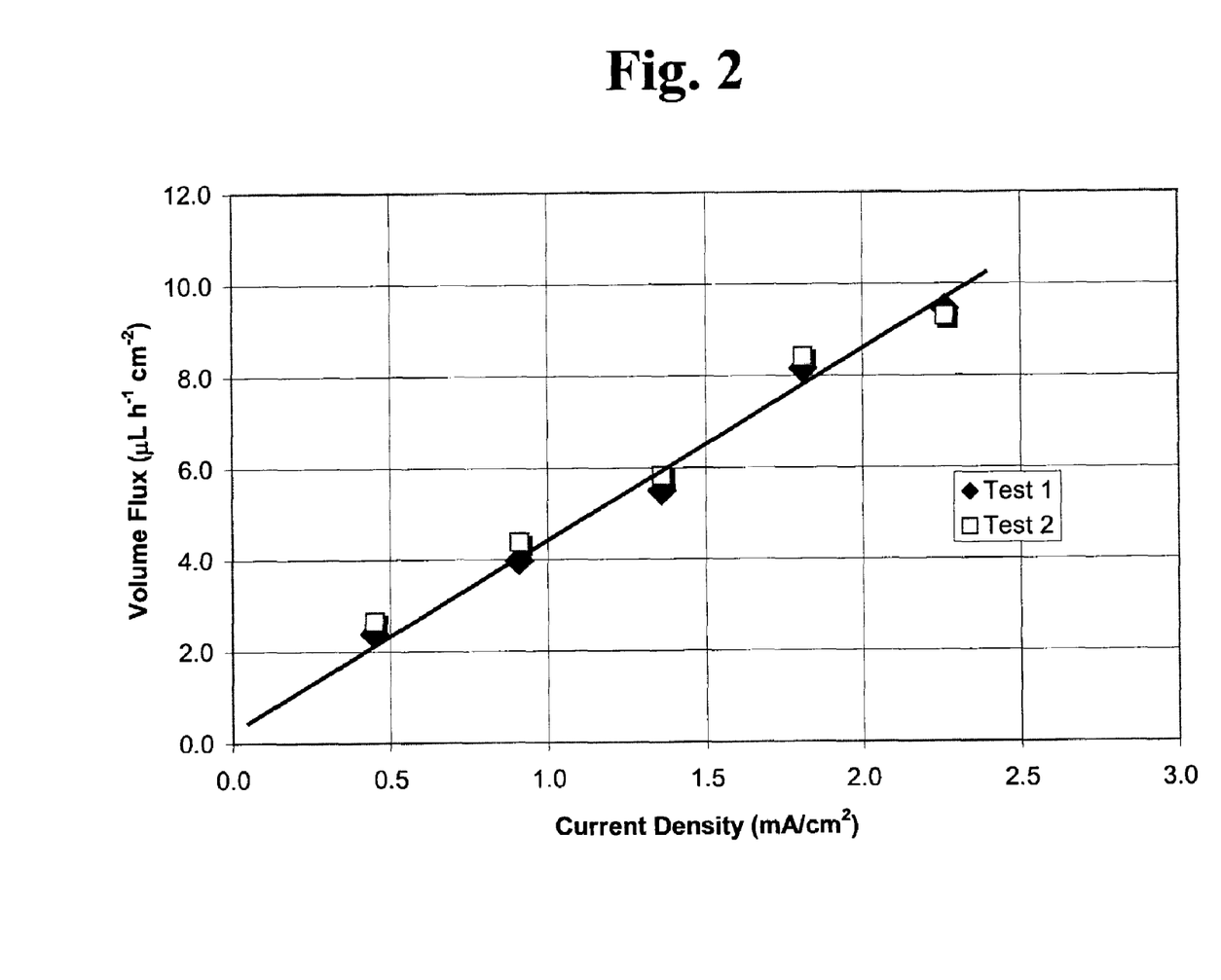
FIG. 2 is a graph of volume flux versus current density in the volume flux range from 2.0 to 10.0 $\mu L\ h^{-1}\ cm^{-2}$ for a fluid delivery device having an anionic exchange membrane fabricated in accordance with the present invention; Cell parameters: AMI 7001 ion exchange membrane, powder zinc anode, nickel mesh cathode, 0.9% NaCl electrolyte.
Figure 3:
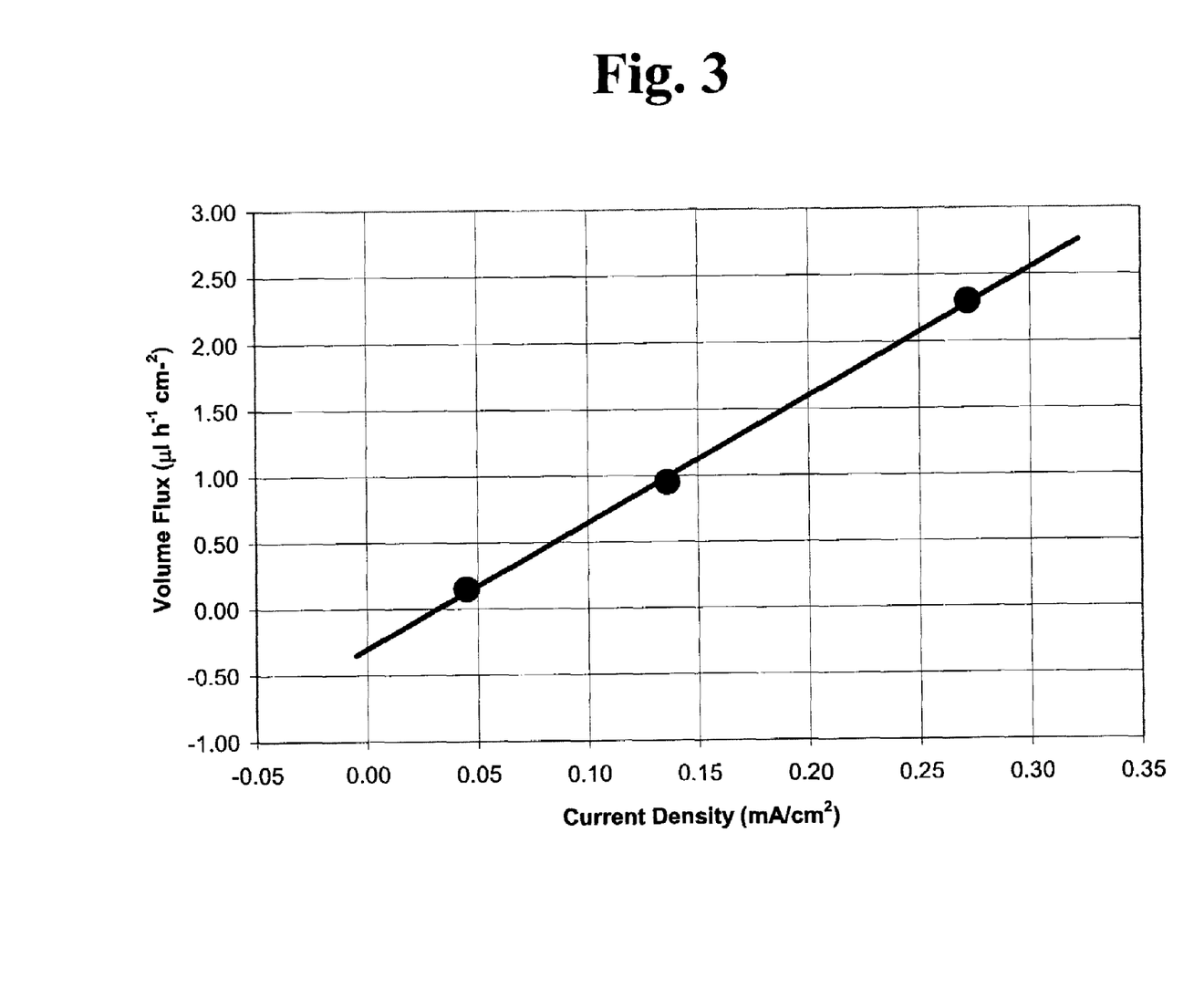
FIG. 3 is a graph of volume flux versus current density in the volume flux range from 0 to 2.5 $\mu L\ h^{-1}\ cm^{-2}$ for a fluid delivery device having an anionic exchange membrane fabricated in accordance with the present invention; Cell parameters: Neosepta® AFN ion exchange membrane, solid zinc anode, silver chloride cathode, 0.9% NaCl electrolyte.
Figure 4:
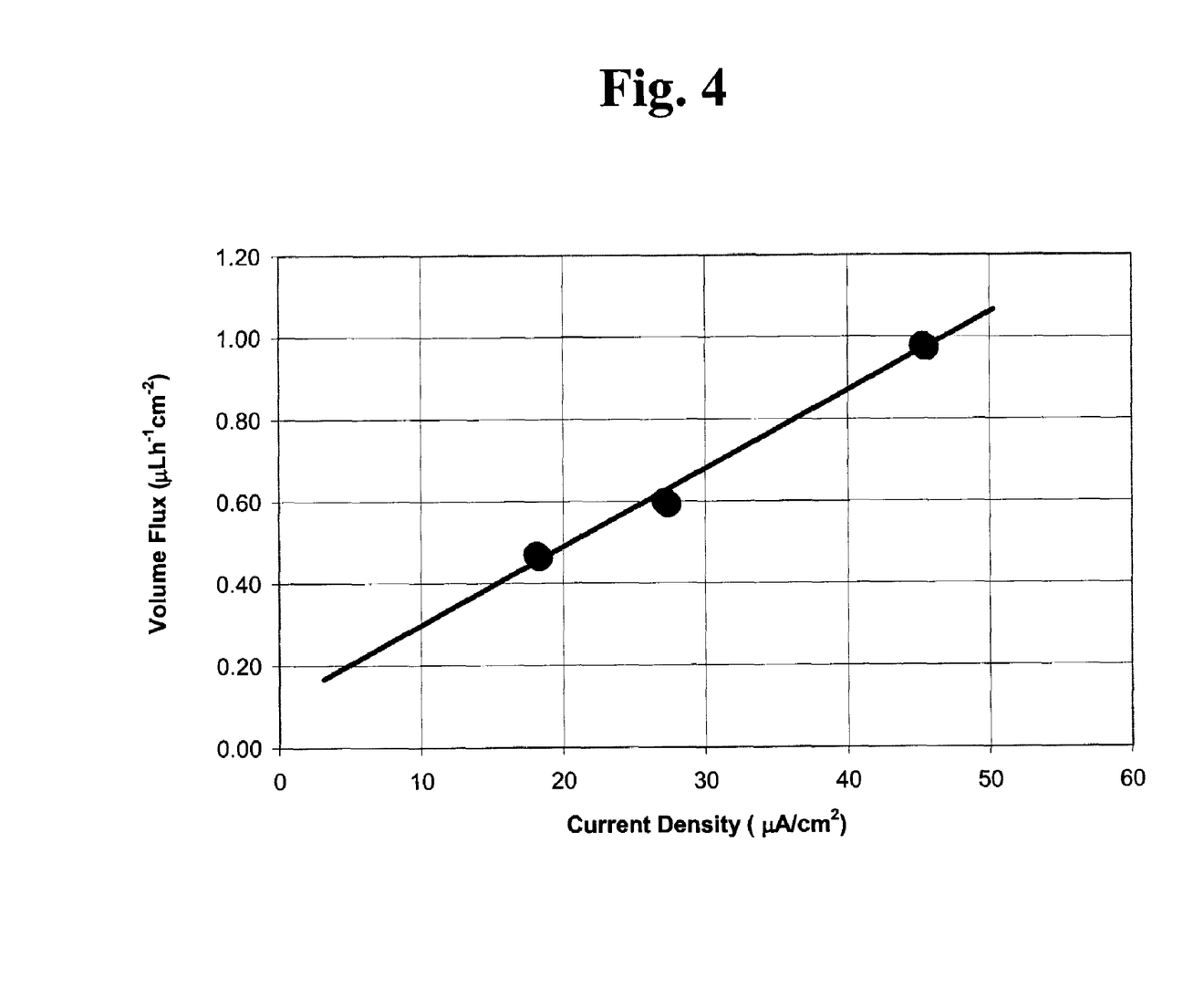
FIG. 4 is a graph of volume flux versus current density in the volume flux range from 0.5 to 2.5 $\mu L\ h^{-1}\ cm^{-2}$ for a fluid delivery device having an anionic exchange membrane fabricated in accordance with the present invention; Cell parameters: Neosepta® AMX ion exchange membrane, solid zinc anode, silver chloride cathode, 0.9% NaCl electrolyte.
Figure 5:
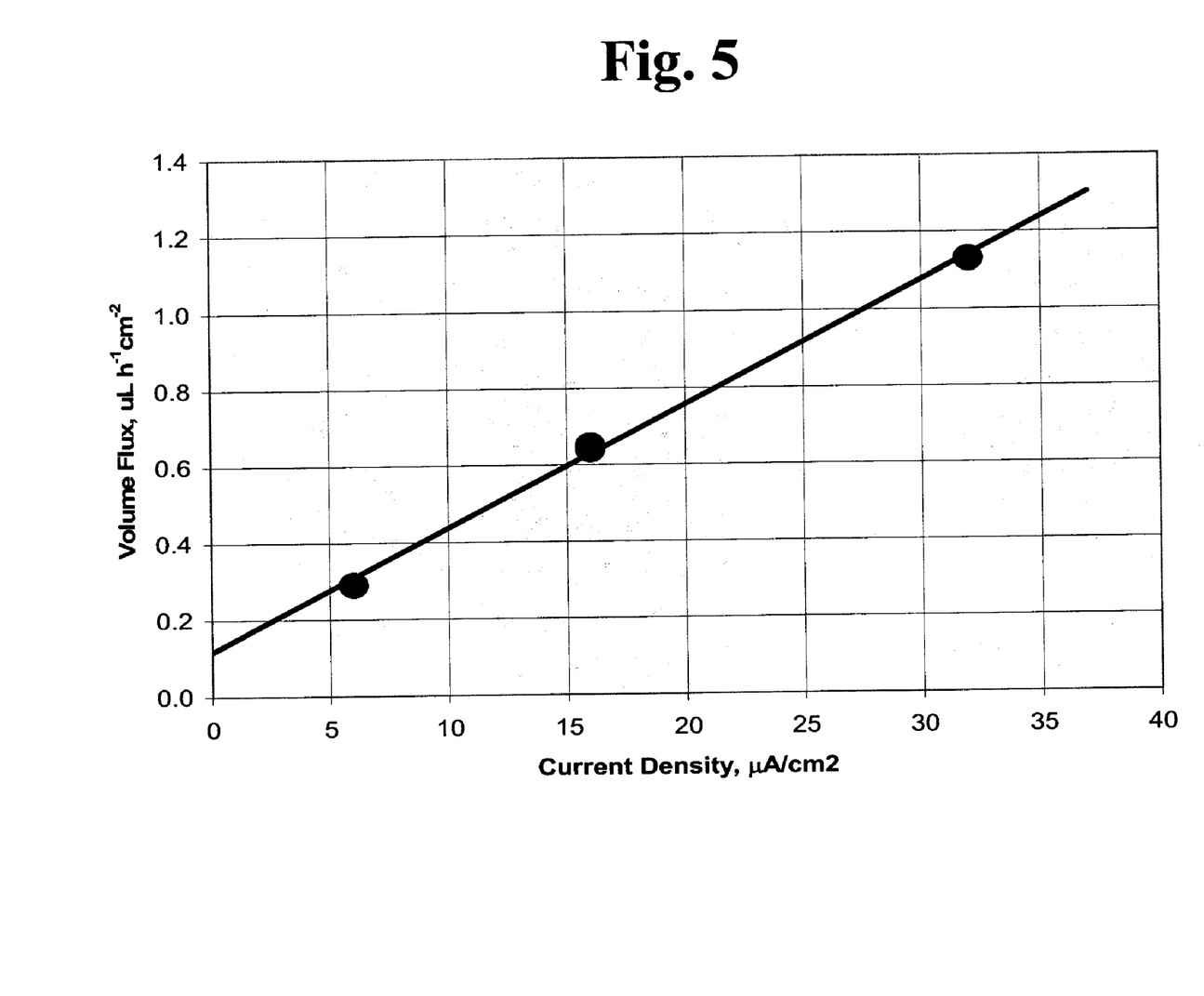
FIG. 5 is a graph of volume flux versus current density in the volume flux range from 0.2 to 1.2 $\mu L\ h^{-1}\ cm^{-2}$ for a fluid delivery device having an cationic exchange membrane fabricated in accordance with the present invention; Cell parameters: NAFION® 117 cation exchange membrane, solid zinc anode, silver chloride cathode, 0.9% NaCl electrolyte.

For the embodiments of the present invention illustrated in the drawings, a linear relationship between volume flux and current density was obtained at high and low volume fluxes. This is illustrated in the case of first embodiment in FIG. 2 for volume flux ranging from 2.0 to 10.0 µL h$^{-1}$ cm$^{-2}$; and in FIG. 3 for volume flux ranging from 0.1 to 2.5 µL h$^{-1}$ cm$^{-2}$. The current density required to produce such volume fluxes depends on the membrane type used and may be as low as 20 µA cm$^{-2}$ to produce a volume flux of 0.5 µL h$^{-1}$ cm$^{-2}$, as shown in FIG. 4. Another feature of the embodiment shown in FIG. 1 is high stability operation over more than 1000 hours of operation.

The foregoing description merely explains and illustrates the invention and the invention is not limited thereto except insofar as the appended claims are so limited, as those skilled in the art that have the disclosure before them will be able to make modifications without departing the scope of the invention.

What is claimed is:

1. A fluid delivery device, comprising:
   an electrochemical pump comprising a first electrode, a second electrode, and an ion exchange membrane positioned therebetween, at least one of said electrodes spaced from said ion exchange membrane, wherein the electrochemical pump is capable of transporting water;
   an electrochemical pump product chamber, wherein the electrochemical pump product chamber is capable of retaining water transported by the electrochemical pump;
   a displaceable member positioned between the electrochemical pump product chamber and a reservoir, wherein the displaceable member is controllably displaced upon transportation of water from the electrochemical pump;
   a reservoir, wherein the reservoir is capable of containing a fluid which is delivered upon displacement of the displaceable member; and,
   a housing for containing the electrochemical pump, the electrochemical pump product chamber, the displaceable member, and the reservoir, said housing configured to allow fluid external to said housing to operably communicate with at least one of said electrodes.

2. The fluid delivery device according to claim 1, wherein the electrochemical pump further comprises an electrical controller.

3. The fluid delivery device according to claim 2, wherein the electrochemical pump further comprises an activation switch, and a support member.

4. The fluid delivery device according to claim 3, wherein the electrochemical pump further comprises a protective porous separator or a protective porous gel that are generally permeable to $H_2O$ molecules or saline.

5. The fluid delivery device according to claim 4, wherein the protective porous separator or protective porous gel comprises a water reservoir or a saline reservoir.

6. The fluid delivery device according to claim 2, wherein the first and second electrodes form a galvanic couple.

7. The fluid delivery device according to claim 2, wherein the ion exchange membrane is either an anionic or cationic ion-exchange type membrane.

8. The fluid delivery device according to claim 1, wherein the displaceable member is selected from the group consisting of a piston, bladder, bellows, diaphragm, plunger, and combination thereof.

9. The fluid delivery device according to claim 1, wherein the reservoir contains a fluid selected from the group consisting of a biological, drug, lubricant, fragrant fluid, chemical agent, and mixtures thereof.

10. The fluid delivery device according to claim 1, wherein the reservoir includes one or more apertures.

11. A fluid delivery device, comprising:
an electrochemical pump, wherein the electrochemical pump is capable of transporting water, and wherein the electrochemical pump includes a first electrode, a second electrode, an ion exchange membrane, and an electrical controller;
an electrochemical pump product chamber, wherein the electrochemical pump product chamber is capable of retaining water transported from the electrochemical pump;
a displaceable member positioned between the electrochemical pump product chamber and a reservoir, wherein the displaceable member is controllably displaced upon transportation of water from the electrical pump;
a reservoir, wherein the reservoir is capable of containing a fluid which is delivered upon displacement of the displaceable member; and,
a housing for containing the electrochemical pump, the electrochemical pump product chamber, the displaceable member, and the reservoir, said housing configured to allow fluid external to said housing to operably communicate with at least one of said electrodes.

12. The fluid delivery device according to claim 11, wherein the electrochemical pump further includes an activation switch, and a support member.

13. The fluid delivery device according to claim 11, wherein the electrochemical pump further includes a protective porous separator or a protective porous gel that are generally permeable to $H_2O$ molecules or saline.

14. The fluid delivery device according to claim 13, wherein the protective porous separator or protective porous gel includes a water reservoir or a saline reservoir.

15. The fluid delivery device according to claim 11, wherein the first and second electrodes form a galvanic couple.

16. The fluid delivery device according to claim 11, wherein the ion exchange membrane is either an anion or cationic ion exchange type membrane.

17. The fluid delivery device according to claim 11, wherein the displaceable member is selected from the group consisting of a piston, bladder, bellows, diaphragm, plunger, and combinations thereof.

18. The fluid delivery device according to claim 11, wherein the reservoir contains a fluid selected from the group consisting of a biological, drug, lubricant, fragrant fluid, chemical agent, and mixtures thereof.

19. The fluid delivery device according to claim 11, wherein the reservoir includes one or more apertures.

20. A fluid delivery device, comprising:
an electrochemical pump, wherein the electrochemical pump is capable of transporting water, and wherein the electrochemical pump comprises:
a protective porous separator or protective porous gel operably attached proximate an end of the fluid delivery device, the protective porous separator or protective porous gel are generally permeable to $H_2O$ molecules or saline;
a first electrode compartment that emanates contiguously from the protective porous separator or the protective porous gel;
a first electrode that emanates contiguously from the first electrode compartment;
an ion exchange membrane that emanates contiguously from the first electrode;
a second electrode that emanates contiguously from the ion exchange membrane;
an electrical controller in electrical communication with the first and second electrodes;
an electrochemical pump product chamber, wherein the electrochemical pump product chamber is capable of retaining water transported from the electrochemical pump;
a displaceable member positioned between the electrochemical pump product chamber and a reservoir, wherein the displaceable member is controllably displaced upon transportation of water from the electrochemical pump, and further wherein the reservoir is capable of containing a fluid delivered upon displacement of the displaceable member; and,
a housing for containing the electrochemical pump, the electrochemical pump product chamber, the displaceable member, and the reservoir, said housing configured to allow fluid external to said housing to operably communicate with at least one of said electrodes.

21. The fluid delivery deice according to claim 20, wherein the electrochemical pump further includes an operably connected activation switch to start and stop the fluid delivery.

22. The fluid delivery device according to claim 20, wherein the electrochemical pump further includes a support member operably attached to the ion-exchange membrane to provide physical support thereto.

23. The fluid delivery device according to claim 20, wherein the protective porous separator or protective porous gel further include a water reservoir or a saline reservoir.

24. The fluid delivery device according to claim 20, wherein the first and second electrodes form a galvanic couple.

25. The fluid delivery device according to claim 20, wherein the ion exchange membrane is either an anionic or cationic ion-exchange type membrane.

26. The fluid delivery device according to claim 20, wherein the displaceable member is selected from the group consisting of a piston, bladder, bellows, diaphragm, plunger, and combinations thereof.

27. The fluid delivery device according to claim 20, wherein the reservoir contains a fluid selected from the group consisting of a biological, drug, lubricant, fragrant fluid, chemical agent, and mixtures thereof.

28. The fluid delivery device according to claim 20, wherein the reservoir includes one or more apertures.

29. The fluid delivery device according to claim 20, wherein the electrical controller facilitates faster fluid delivery start-up, shut-off, and adjustability of the fluid-delivery rate.

30. The fluid delivery device according to claim 29, wherein the electrical controller is an electrical circuit.

31. The fluid delivery device according to claim 30, wherein the electrical controller provides varied delivery profiles including pulsing.

32. The fluid delivery device according to claim 29, wherein the electrical controller provides varied delivery profiles including pulsing.

33. The fluid delivery device according to claim 20 wherein the electrical controller is controlled remotely.

34. A process for delivering a fluid, comprising the steps of:
providing a fluid delivery device having an electrochemical water-transporting pump supported by a housing;
transporting water from outside the housing using the electrochemical water transporting pump at a rate proportional to an electrical controller signal output; thereby expanding a volume of an electrochemical pump product chamber;
generating sufficient pressure from the expanded electrochemical pump product chamber; and,
displacing a displaceable member, and, in turn, controllably expelling fluid from the fluid delivery device.

35. The process according to claim 34 further comprising adjusting a fluid delivery rate profile.

36. The process according to claim 34 further comprises adjusting a fluid delivery rate.

37. The process according to claim 36 wherein adjusting a fluid delivery rate comprises changing thee electrical controller signal output.

38. The process according to claim 34, further comprising:
providing a switch operably coupled between a first electrode and a second electrode; and,
controlling fluid delivery by activating the switch.

* * * * *